(12) United States Patent
McCormick et al.

(10) Patent No.: US 7,498,176 B2
(45) Date of Patent: Mar. 3, 2009

(54) MICROARRAY WITH HYDROPHOBIC BARRIERS

(75) Inventors: Mark McCormick, Madison, WI (US); Klaus-Peter Stengele, Pleiskirchen (DE); Gary Barrett, Madison, WI (US); Roland Green, Madison, WI (US)

(73) Assignee: Roche Nimblegen, Inc., Madison, WI (US)

( * ) Notice: Subject to any disclaimer, the term of this patent is extended or adjusted under 35 U.S.C. 154(b) by 0 days.

(21) Appl. No.: 10/673,760

(22) Filed: Sep. 29, 2003

(65) Prior Publication Data

US 2004/0110211 A1    Jun. 10, 2004

Related U.S. Application Data

(60) Provisional application No. 60/414,777, filed on Sep. 27, 2002.

(51) Int. Cl.
*G01N 1/10* (2006.01)
(52) U.S. Cl. .................................... 436/180
(58) Field of Classification Search ............... 422/61, 422/68.1, 99, 101, 100; 436/94, 174, 180; 435/6
See application file for complete search history.

(56) References Cited

U.S. PATENT DOCUMENTS

| | | | |
|---|---|---|---|
| 5,143,854 A | 9/1992 | Pirrung et al. | |
| 5,252,743 A | 10/1993 | Barrett et al. | |
| 5,384,261 A | 1/1995 | Winkler et al. | |
| 5,412,087 A | 5/1995 | McGall et al. | |
| 5,665,975 A | 9/1997 | Kedar | |
| 5,677,195 A | 10/1997 | Winkler et al. | |
| 5,885,837 A | 3/1999 | Winkler et al. | |
| 5,981,956 A | 11/1999 | Stern | |
| 6,028,189 A * | 2/2000 | Blanchard | 536/25.3 |
| 6,090,555 A | 7/2000 | Fiekowsky et al. | |
| 6,210,894 B1 * | 4/2001 | Brennan | 435/6 |
| 6,242,180 B1 | 6/2001 | Chee | |
| 6,346,413 B1 | 2/2002 | Fodor et al. | |
| 6,355,419 B1 * | 3/2002 | Alfenito | 435/6 |
| 6,368,799 B1 | 4/2002 | Chee | |
| 6,375,903 B1 | 4/2002 | Cerrina et al. | |
| 6,399,365 B2 | 6/2002 | Besemer et al. | |
| 6,403,317 B1 | 6/2002 | Anderson | |
| 6,403,957 B1 | 6/2002 | Fodor et al. | |
| 6,406,844 B1 | 6/2002 | Pirrung et al. | |
| 6,544,739 B1 | 4/2003 | Fodor et al. | |
| 6,589,726 B1 * | 7/2003 | Butler et al. | 435/4 |
| 6,770,441 B2 * | 8/2004 | Dickinson et al. | 435/6 |
| 6,864,052 B1 * | 3/2005 | Drmanac et al. | 435/6 |
| 2004/0044195 A1 * | 3/2004 | Kwiatkowski | 536/25.3 |
| 2004/0101949 A1 * | 5/2004 | Green et al. | 435/287.2 |

* cited by examiner

*Primary Examiner*—Jill Warden
*Assistant Examiner*—Dwayne K Handy
(74) *Attorney, Agent, or Firm*—Quarles & Brady LLP

(57) ABSTRACT

The present invention is a microarray having a plurality of subarrays with a hydrophobic barrier that defines each subarray of the microarray, and a method for preparing such a microarray. The hydrophobic barrier is prepared using a microarray synthesis instrument, where NPPOC photoprotected and other hydrophobic group-bearing phosphoramidites are coupled to the microarray using light from a digital micromirror to direct formation of the hydrophobic barrier. The method utilizes hydrophobicity, a well-established property, of conventional phosphoramidite protecting groups for an entirely new application, the synthesis of hydrophobic barriers on microarrays.

6 Claims, 4 Drawing Sheets

US 7,498,176 B2

MICROARRAY WITH HYDROPHOBIC BARRIERS

CROSS-REFERENCE TO RELATED APPLICATIONS

This application claims the benefit of U.S. Provisional Patent Application Ser. No. 60/414,777, filed on Sep. 27, 2002.

STATEMENT REGARDING FEDERALLY SPONSORED RESEARCH OR DEVELOPMENT

Not applicable.

BACKGROUND OF THE INVENTION

DNA microarray technology has been applied to many areas such as gene expression and discovery, mutation detection, allelic and evolutionary sequence comparison, genome mapping and more. Unfortunately, most applications fail to tap into the full capacity of microarray technology as many hybridization assays involve far less probes than are available using the full capability of the number of features possible in a high-density microarray.

The advent of DNA microarray technology makes it possible to build an array of hundreds of thousands of DNA sequences in a very small area, such as the size of a microscopic slide. See, e.g., U.S. Pat. No. 6,375,903 and U.S. Pat. No. 5,143,854, each of which is hereby incorporated by reference in its entirety. The disclosure of U.S. Pat. No. 6,375,903 enables the construction of so-called maskless array synthesizer (MAS™) instruments in which light is used to direct synthesis of the DNA sequences, the light direction being performed using a digital micromirror device (DMD). Using an MAS™ instrument, the selection of DNA sequences to be constructed in the microarray is under software control so that individually customized arrays can be built to order. In general, MAS™ based DNA microarray synthesis technology allows for the parallel synthesis of over 800,000 unique oligonucleotides in a very small area of on a standard microscope slide. For many applications, the entirety of the synthesized array is devoted to the evaluation of one sample of test nucleic acids (i.e., RNA or DNA). In these applications, the entire microarray area is enclosed in a small chamber so as to allow for the application of the single sample, thus providing a very efficient means for measuring the concentration of a very large number of nucleic acid molecules within that one sample. A typical application of this sort is gene expression profiling.

In applications where a smaller number of genes are being studied, or where a reduced set of probes will be queried for each sample, the microarray can be logically divided into any number of smaller arrays (i.e., subarrays) each having the same or different nucleotide probes, a concept sometimes referred to as an array of arrays. To use an array of arrays efficiently, multiple samples are hybridized in parallel, in a single experiment, with each sample being hybridized to a given and known subarray in the array of arrays. This parallel loading strategy provides for efficient utilization of the high synthesis capacity of the microarray. In order to load multiple samples onto an array or an array of arrays and avoid sample cross-contamination, some mechanism must be provided to sequester each sample from adjacent samples. Currently, microarrays built for this purpose (e.g., U.S. Pat. No. 5,874,219) use physical wells to separate probe sets for different samples. This approach, however, requires the user to know precisely where the array has been synthesized on the slide in order to properly place the barriers forming the well walls. Alternatively, the user could compensate for the ambiguity by reducing the dimensions of the subarrays in order to allow for error in barrier placement. This is not an ideal approach since it wastes synthetic capacity in the interest of enclosing a full experimental set of features within each subarray.

BRIEF SUMMARY OF THE INVENTION

The present invention is summarized as a microarray having a hydrophobic barrier area that separates and defines subarrays on the microarray. The concept behind the invention is to provide hydrophobic barriers around a microarray so as to inhibit cross-contamination of fluids between subarrays on an array, when conducting multiple sample assays. The method for synthesizing the barriers surrounding microarrays utilizes hydrophobicity, a well-established property of for example, the trityl protecting group of conventional phosphoramidites for an entirely new application. In general, the method employs the step of coupling the barrier areas on the microarray with hydrophobic group-bearing phosphoramidites, such as trityl-protected phosphoramidite, under conditions where a deblocking step is not performed.

Accordingly, one aspect of the present invention provides for a microarray having a substrate on which are arranged a plurality of subarrays, wherein each subarray on the microarray is surrounded by a hydrophobic barrier, which separates each subarray from an adjacent subarray and wherein the hydrophobic barrier inhibits fluid communication between each subarray of the microarray. Also, another aspect of the present invention provides for a method for preparing a microarray having a hydrophobic barrier defining a plurality of subarrays on the microarray, where the method includes: selecting at least one probe set comprising probes of interest; synthesizing the probe sets on a microarray slide to provide the plurality of subarrays; depositing between each of the subarrays a hydrophobic group-bearing phosphoramidite to provide a hydrophobic barrier which surrounds each subarray; and inhibiting fluid communication between each of the subarrays on the microarray.

A further aspect of the present invention provides that a slide containing the array of arrays may be held in the identical position throughout synthesis of both the oligonucleotides and the hydrophobic barrier. Thus, synthesized barriers could be placed immediately adjacent to synthesized features on a subarray allowing the use of all potential synthesis sites within the barrier-enclosed area, referred to as a subarray.

DETAILED DESCRIPTION OF THE INVENTION

The present invention is a microarray having a hydrophobic barrier area that separates and defines the subarrays of the microarray. The hydrophobic barrier is constructed using a MAS™ microarray onto the substrate of the microarray and without prior special treatment of the substrate. A digital micromirror device (DMD) is used to direct light to the location of the hydrophobic barrier.

Figure 1:
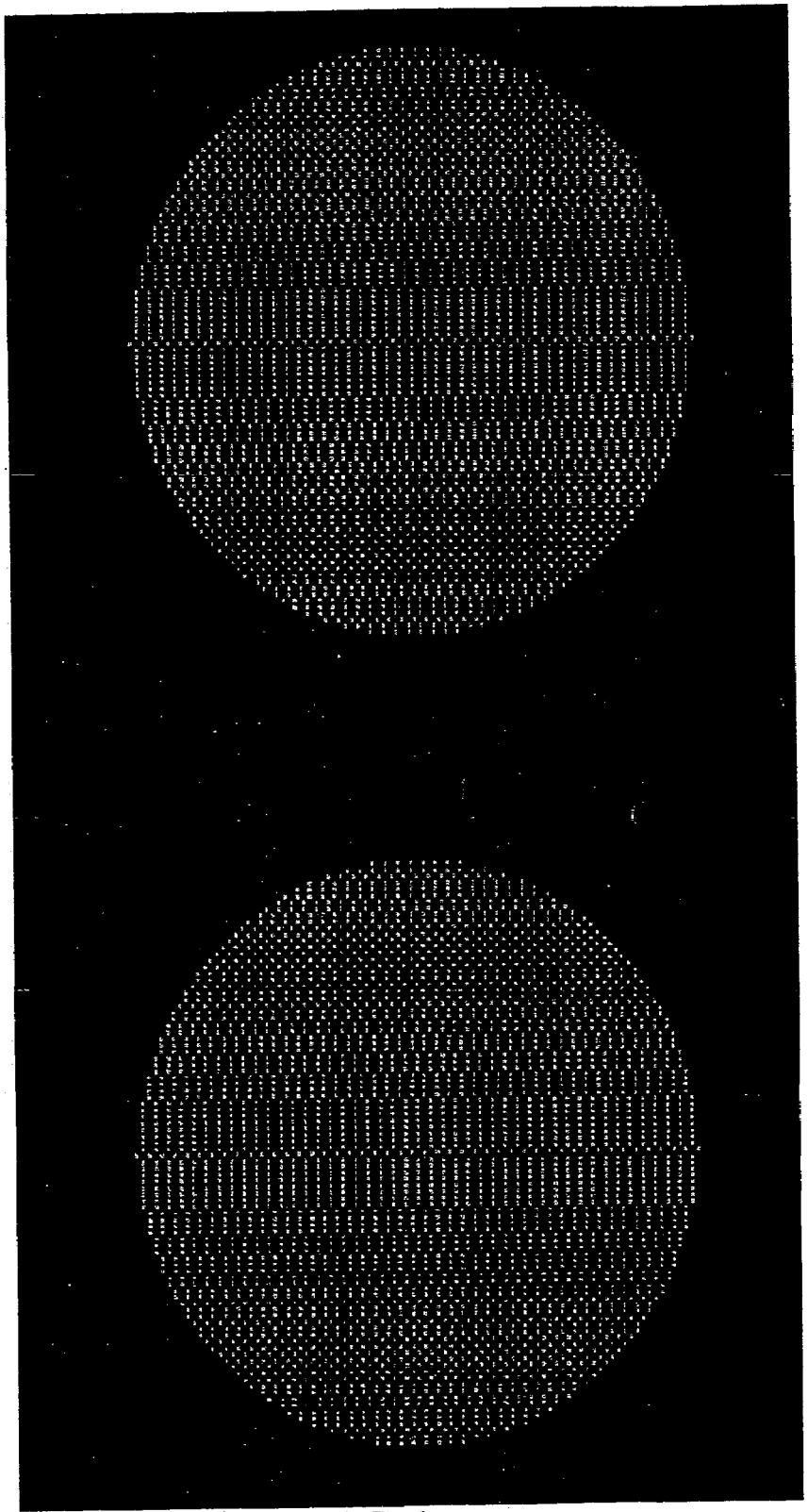
FIG. 1 is an illustration of two subarrays formed on a microarray and the blackened hydrophobic barrier that surrounds each subarray.
Figure 2:
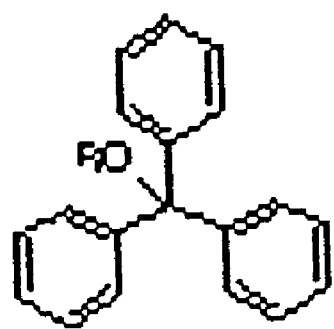
FIG. 2 is an illustration of a trityl core group.

In one method, a uniform layer of NPPOC (2-(2 nitro phenyl) propoxy carbonyl) protected phosphoramidite is coupled across the entirety of the array surface and individual subarrays are synthesized in the desired arrangement. Regions where hydrophobic groups are desired are selectively photo-deprotected, and conventional trityl (Dimethoxytrityl) protected groups or other phosphoramidites bearing hydrophobic groups are coupled to the barrier area on the microarray. The barrier areas are coupled with trityl-protected phosphoramidite under conditions where a deblock step is not performed. The method utilizes a well-established hydrophobic property of the trityl moiety, shown in FIG. 2, on the trityl protecting group of conventional phosphoramidites for an entirely new application, the synthesis of hydrophobic barriers on microarrays. The result is a grid of subarrays around each subarray where each subarray is separate from an adjacent subarray by a barrier of hydrophobic group-bearing phosporamidites.

As described above, in practice, the method is only a slight variation on the normal microarray synthesis process. This characteristic allows the hydrophobic barrier to be constructed in place by the MAS™ instrument itself without prior treatment of the substrate. The normal method of microarray synthesis is initiated by the synthesis of a short DNA-based linker sequence over the entirety of the available array surface. In the new method described here, the areas of a microarray are separated into two basic types of areas: hydrophilic subarrays (containing probe sets from 1 to hundreds of thousands) and hydrophobic barrier areas.

To understand this concept, the introduction of some terminology is helpful. For the purpose of the present invention, a subarray is an area on the microarray containing a plurality of features in which a number of nucleic acid probes, a set of probes of interest are all anchored. In general, subarrays may vary in size depending upon the number of probes of interest included in each probe set. The size of the subarrays is determined by the number of features combined in a single subarray area and the number of micromirror device elements assigned to each feature of the subarray on a microarray. Features are the individual probe synthesis areas: 1 feature=1 probe=1 (or more) mirrors. For purposes of this invention one can dynamically assign 1 or more mirrors to a feature in the array design and the terminology used is 1:4 meaning 1 mirror for the probe, four mirrors for the feature. Thus, 1024×768=786432 mirrors/4 mirror per feature=196608 features/array. 1:1 would be 786432 features. A subarray may also contain blank positions (a position available for a probe but is left with no probe). For the purpose of the present invention, the shape of each subarray does not matter and may vary.

Figure 3:
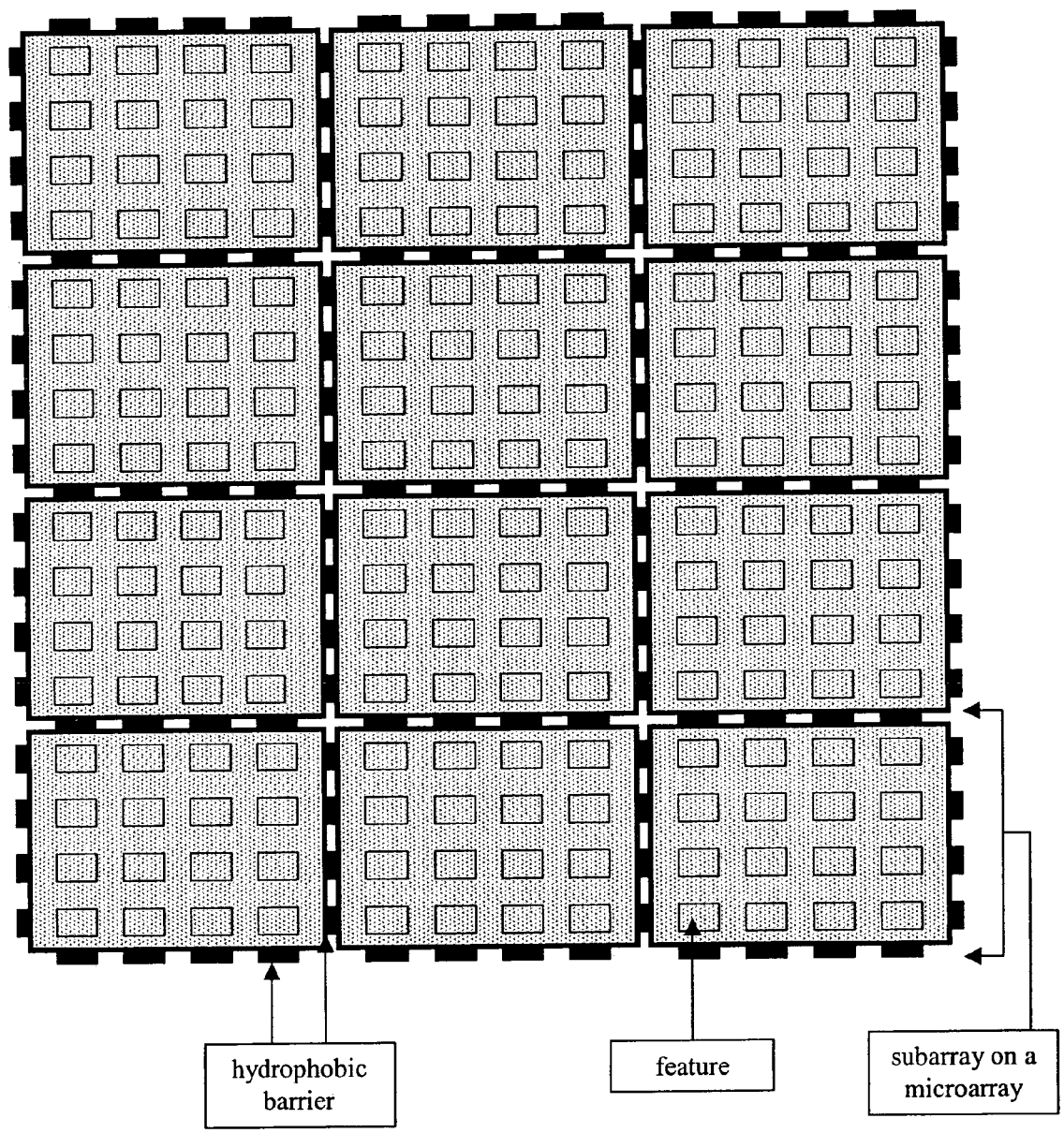
FIG. 3 is a schematic of a plurality of subarrays on a microarray and the hydrophobic barrier surrounding each subarray.
Figure 4:
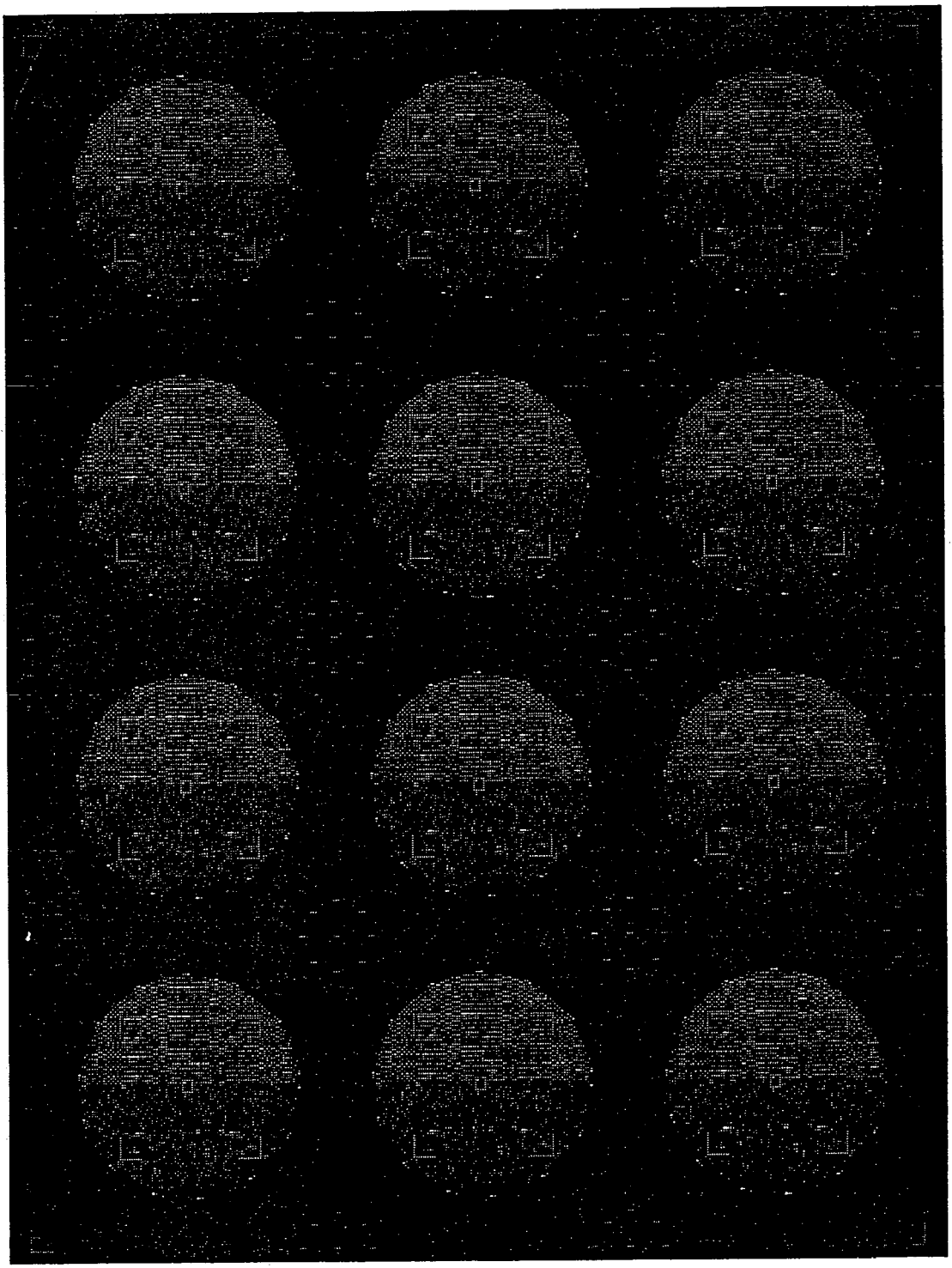
FIG. 4 is an illustration of a plurality of subarrays on a microarray and the blackened hydrophobic barrier that surrounds each subarray.

The barrier area is the space that immediately surrounds the subarray. The barrier area separates and defines each subarray in the microarray by forming a hydrophobic barrier around each subarray or sample area. The hydrophobic barrier is flexibly deployable within the array and can be placed with great precision immediately adjacent to and surrounding the subarray areas. Thus, by coupling hydrophobic group-bearing phosphoramidites to the barrier area, the area surrounding the subarray is able to then provide a hydrophobic barrier to inhibit fluid communication between subarrays during hybridization of the subarrays to sample(s). The hydrophobic barrier is typically coupled last during synthesis and has no impact on how the array synthesis is performed, apart from the addition of the trityl coupling step. The hydrophobic barrier is used to contain individual samples during the use of the array in a hybridization to samples. Accordingly, suitable operations may include hybridization assays, where the hydrophobic barrier would prevent cross-contamination between individual subarray hybridizations on a microarray. Using the technique described here, ultimately a set of features of a subarray are compartmentalized by hydrophobic barriers from other features of other subarrays on a microarray, as shown in FIGS. 3 and 4.

To build the hydrophobic barrier in the microarray, barrier areas are coupled with a hydrophobic group-bearing phosphoramidites, such as a trityl-protected phosphoramidite, under conditions where a deblock step is not performed. In the preferred embodiment, this step is performed following the coupling of the NPPOC-protected phosphoramidite to the array area during routine microarray synthesis.

Therefore the first synthesis step is the coupling of an NPPOC protected phosphoramidite everywhere on the array. The NPPOC is the photoprotecting group that allows for patterning with the mirror array. The probes are synthesized in their grid and the hydrophobic areas are left unexposed to light (therefore protected) until the completion of synthesis when they are deprotected (by light) and trityl-phosphoramidite is coupled only in these regions. The NPPOC-T is used as a patternable initial layer but any NPPOC (or other photoprotected phosphoramidite) would work. The NPPOC is necessary but not sufficient for the invention in that it is actually the trityl group that is providing the hydrophobicity (as might any other hydrophobic moiety protected phosphoramidite) but the NPPOC is allowing for photopatterning.

Linker sequences, on the other hand, are synthesized in subarray areas where features will be synthesized. Linkers are short molecules (typically but not necessarily oligonucleotides) used to place the probe molecules further off the array surface to improve their accessibility in solution thereby improving hybridization kinetics. The result is a plurality or grid of subarrays where every subarray in the grid is surrounded by barriers consisting of hydrophobic group-bearing phosphoramidites. During subsequent array hybridization operations, the hydrophobic barriers surrounding each subarray are left intact, preventing fluid communication between the individual subarrays on the microarray during subsequent operations.

The invention will now be detailed by means of the following example.

EXAMPLE

Building Hydrophobic Barriers Surrounding Subarrays

The photolabile phosphoramidite protecting group, NPPOC-T was coupled to the entire array surface under standard coupling conditions well known in the art of oligonucleotide and in situ array synthesis. In order to carry out the inventive method, care is taken to ensure that there is appropriate spacing, suitably at least between 4 to 7 mirror wide lanes (60-120 µm), and optionally longer spacing is suitable. The probe subarrays are synthesized by the MAS™ instrument according to the method described herein. The area to be a barrier is deprotected using the digital mirror devices of the MAS™ microarray synthesis instrument. The trityl phosphoramidite (protected phosphoramidite) is then coupled to the barrier areas also using methods well known to one skilled in the art. A deblocking step is not performed. The entire array is deprotected under conditions that do not remove the trityl moiety. The deprotection conditions are used for all suitable arrays. These conditions do not remove the trityl group while they do remove all side chain protecting groups on the synthesized probes in the array. The result is a microarray on which are arranged a plurality of subarrays surrounded by a hydrophobic barrier inhibiting fluid communication between each subarray of the microarray during an assay.

The present invention is most useful for an application in which a hybridization assay is used to analyze a large number of samples for example. Suitable applications may include toxicogenomic screening of drug candidates, SNP scoring, and targeted resequencing among others. It is understood, however, that examples and embodiments of the present invention set forth above are illustrative and not intended to confine the invention. The invention embraces all modified forms of the examples and embodiments as come within the scope of the following claims.

We claim:

1. A method for preparing a microarray having a hydrophobic barrier defining a plurality of subarrays on the microarray, the microarray constructed by a light-directed maskless array synthesizer instrument, the method comprising the steps of:
   a) selecting at least one probe set comprising probes of interest;
   b) synthesizing the probe sets selected in step a) on a microarray slide to provide the plurality of subarrays using the light-directed maskless array synthesizer instrument;
   c) depositing between each of the subarrays synthesized in step b) a hydrophobic group-bearing phosphoramidite to provide a hydrophobic barrier which surrounds each subarray, wherein the deposit of the hydrophobic barrier is made by using the same light-directed maskless array synthesizer instrument used in step b); and
   d) inhibiting fluid communication between each of the subarrays on the microarray.

2. The method of claim 1 wherein hydrophobic barrier is synthesized using a hydrophobic group-bearing phosphoramidite.

3. The method of claim 2 wherein the phosphoramidite is a trityl protected phosphoramidite.

4. A method for preparing a microarray having a hydrophobic barrier defining a plurality of subarrays on the microarray, wherein a substrate containing the microarray is held in the identical position by a light-directed maskless array synthesizer instrument throughout the method, the method comprising the steps of:
   a) selecting at least one probe set comprising probes of interest;
   b) synthesizing the probe sets selected in step a) on a microarray slide using the light-directed maskless array synthesizer instrument to provide the plurality of subarrays; and
   c) depositing between each of the subarrays synthesized in step b) a hydrophobic group-bearing phosphoramidite to provide a hydrophobic barrier which surrounds each subarray, wherein the deposit of the hydrophobic barrier is made by using the same light-directed maskless array synthesizer instrument used to synthesize the probe sets of step b), and wherein the substrate containing the microarray is held in the identical position by the instrument throughout each step of the method.

5. The method of claim 4 wherein hydrophobic barrier is synthesized using a hydrophobic group-bearing phosphoramidite.

6. The method of claim 5 wherein the is a trityl protected phosphoramidite.

* * * * *